US007567647B1

(12) United States Patent  
Maltz (10) Patent No.: US 7,567,647 B1  
(45) Date of Patent: Jul. 28, 2009

(54) SOURCE ARRAY TRANSLATION FOR DIGITAL TOMOSYNTHESIS

(75) Inventor: Jonathan S. Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/101,803

(22) Filed: Apr. 11, 2008

(51) Int. Cl.
*A61B 6/00* (2006.01)

(52) U.S. Cl. .............................. 378/21; 378/62; 378/65

(58) Field of Classification Search .................. 378/9, 378/11, 21–27, 62, 65, 98.11, 98.12
See application file for complete search history.

(56) References Cited

U.S. PATENT DOCUMENTS

2009/0022264 A1 * 1/2009 Zhou et al. ..................... 378/5

* cited by examiner

*Primary Examiner*—Courtney Thomas (57) ABSTRACT

A system includes emission of first radiation from a plurality of radiation sources disposed in a fixed relationship to each other, the first radiation emitted from a first plurality of locations defining a first array geometry. A first set of projection images is acquired based on the emitted first radiation and digital tomosynthesis is performed on the first set of projection images to generate a first cross-sectional image. Second radiation is emitted from the plurality of radiation sources disposed in the fixed relationship to each other, the second radiation emitted from a second plurality of locations defining a second array geometry. A second set of projection images is acquired based on the emitted second radiation, and digital tomosynthesis is performed on the second set of projection images to generate a second cross-sectional image. The first array geometry and the second array geometry differ in at least one of shape and size.

18 Claims, 5 Drawing Sheets

SOURCE ARRAY TRANSLATION FOR DIGITAL TOMOSYNTHESIS

BACKGROUND

1. Field

The embodiments described below relate generally to systems for delivering radiation treatment. More specifically, some embodiments are directed to treatment verification systems used in conjunction with such delivery.

2. Description

Radiation treatment plans are designed to maximize radiation delivered to a target while minimizing radiation delivered to healthy tissue. These goals might not be achieved if the radiation is not delivered exactly as specified by the treatment plan. More specifically, errors in radiation delivery can result in low irradiation of tumors and high irradiation of sensitive healthy tissue.

Delivery errors may arise from many sources. For example, a patient position may vary from that designated by a treatment plan, and/or internal patient anatomy may be displaced with respect to external visible markers. Current trends point to hypofractionated delivery in which high doses are delivered per each treatment fraction. These trends increase the necessity of positioning of the patient such that the target coincides with the isocenter of the radiation delivery device during any given treatment.

Commonly-assigned co-pending U.S. Patent Application No. 60/995,828 which is hereby incorporated by reference for all purposes, describes a system to verify a patient position prior to radiation delivery using tomographic images. The tomographic images are generated by a radiation detector which successively receives radiation from several radiation sources disposed in a fixed relationship relative to one another.

The field of view about the patient isocenter and the tomographic angular sampling range of such a system are determined by the relative locations of the radiation detector, the radiation sources and the isocenter. Generally, moving the radiation sources apart (i.e., away from the central radiation beam axis) will increase the angular sampling range (and the depth resolution of the resulting tomographic image) but decrease the field of view. Conversely, decreasing the source spacing will decrease the angular sampling range and increase the field of view.

A system's particular geometric arrangement of radiation sources, detector, and isocenter provide one characteristic field of view and one characteristic angular sampling range. These characteristics may reflect a compromise between conflicting imaging requirements of the various intended uses of the system. This compromise may be further constrained by detector size limitations and tight clearances between system elements.

In view of the foregoing, what is needed is a radiation treatment system to efficiently provide digital tomosynthesis having a first field of view and angular sampling range, and at least a second field of view and angular sampling range. The first field of view and angular sampling range may be suitable for one radiation treatment scenario and the second field of view and angular sampling range may be suitable for another radiation treatment scenario.

SUMMARY

To address at least the foregoing, some embodiments provide a system, method, apparatus, and means to emit first radiation from a plurality of radiation sources disposed in a fixed relationship to each other, the first radiation emitted from a first plurality of locations defining a first array geometry, to acquire a first set of projection images based on the emitted first radiation, and to perform digital tomosynthesis on the first set of projection images to generate a first cross-sectional image. Also included are emission of second radiation from the plurality of radiation sources disposed in the fixed relationship to each other, the second radiation emitted from a second plurality of locations defining a second array geometry, acquisition of a second set of projection images based on the emitted second radiation, and performance of digital tomosynthesis on the second set of projection images to generate a second cross-sectional image. The first array geometry and the second array geometry differ in at least one of shape and size.

In some aspects, emission of the second radiation includes successive emission of a radiation beam from one or more of the second plurality of locations, movement of the plurality of radiation sources disposed in the fixed relationship to each other, and successive emission of a radiation beam from one or more other ones of the second plurality of locations, wherein acquisition of the second set of projection images includes acquisition of one projection image based on each radiation beam successively emitted from the second plurality of locations.

Further to the foregoing aspect, emission of the first radiation may include successive emission of a radiation beam from one or more of the first plurality of locations, movement of the plurality of radiation sources disposed in the fixed relationship to each other, and successive emission of a radiation beam from one or more other ones of the first plurality of locations, wherein acquisition of the first set of projection images comprises acquisition of one projection image based on each radiation beam successively emitted from the first plurality of locations.

According to some aspects, the second set of projection images is acquired with a radiation detector that is maintained in a fixed position during acquisition of the second set of projection images.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by the inventor for carrying out the described embodiments. Various modifications, however, will remain readily apparent to those in the art.

Figure 1:
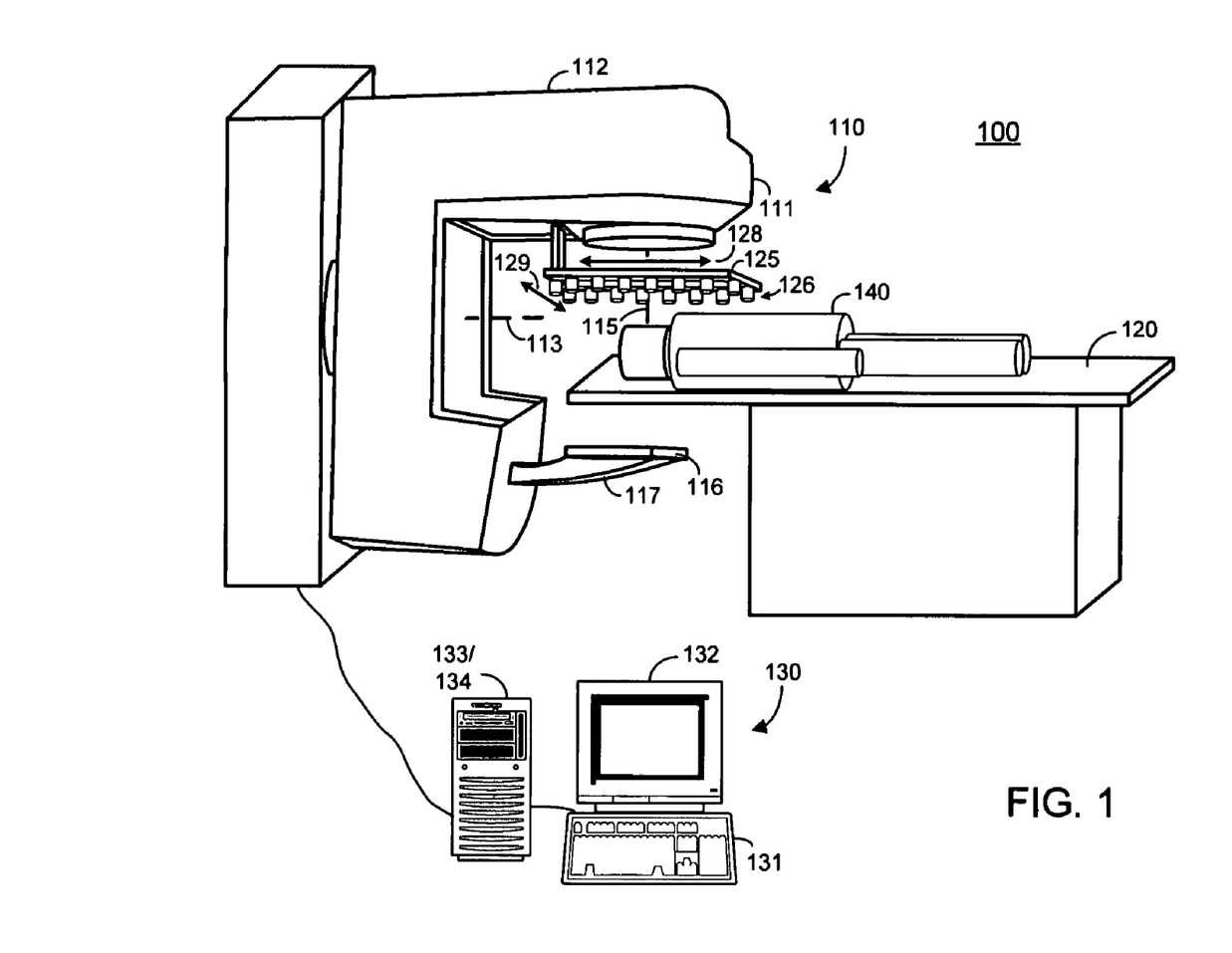
FIG. 1 is a perspective view of a radiation treatment room according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver a treatment beam of x-rays to a target volume of beam object 140. In this regard, beam object 140 may comprise a patient positioned to receive the treatment beam according to a radiation treatment plan. The elements of treatment room 100 may be employed in applications other than those described herein.

Linac 110 may comprise a megavoltage radiotherapy delivery system, but embodiments are not limited thereto. Linac 110 generates and emits a treatment radiation beam from treatment head 111. Treatment head 111 includes a beam-emitting device for emitting a radiation beam during calibration, verification, and/or treatment. The radiation beam may comprise electron, photon or any other type of radiation. According to some embodiments, the beam exhibits energies in the megavoltage range (i.e. >1 MeV) and may therefore be referred to as megavoltage beam.

Also included within treatment head 111 is a beam-shielding device, or collimator, for shaping the beam and for shielding sensitive surfaces from the beam. The collimator may be rotated and various elements of the collimator may be positioned according to a treatment plan. The collimator may thereby control a cross-sectional shape of the beam.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment, treatment head 111 emits a divergent beam of megavoltage x-rays. The beam is emitted towards an isocenter of linac 110. The isocenter is located at the intersection of beam axis 115 and gantry axis 113.

Due to divergence of the beam and the shaping of the beam by the aforementioned beam-shaping devices, the beam may deliver radiation to a volume of beam object 140 rather than only through the isocenter.

Table 120 supports beam object 140 during radiation treatment. Table 120 may be adjustable to assist in positioning a target area of beam object 140 at the isocenter of linac 110. Table 120 may also be used to support devices used for such positioning, for calibration and/or for verification.

Detector 116 may acquire projection images before, during and/or after radiation treatment. For example, detector 116 may be used to acquire projection images for verification and recordation of a target volume position and of an internal patient portal to which radiation is delivered. Detector 116 may comprise any system to acquire an image based on received radiation. Detector 116 may be attached to gantry 112 in any manner, including via extendible and retractable housing 117.

In some embodiments, detector 116 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

Detector 116 may comprise other types of imaging devices. For example, incoming radiation may also be converted to and stored as electrical charge without use of a scintillator layer. In such imaging devices, radiation is absorbed directly by an array of amorphous selenium photoconductors. The photoconductors convert the radiation directly to stored electrical charge that comprises an acquired image of a radiation field.

Translation stage 125 is coupled to gantry 112. Translation stage 125 includes an array of radiation sources 126. Radiation sources 126 may comprise any sources to emit kilovoltage radiation or other imaging radiation that is or becomes known. In some embodiments, radiation sources 126 employ carbon nanotube-based radiation emission. Radiation sources 126 are affixed to translation stage 125 such that each radiation source 126 is disposed in a fixed relationship to each other radiation source 126.

Translation stage 125 is capable of movement in the directions indicated by arrows 128 and 129. These directions may represent the X-direction and Y-direction, respectively, with the Z-direction oriented in the direction of beam axis 115. Translation stage 125 may be movable in the Z-direction in some embodiments. In this regard, translation stage 125 may be selectively deployed from a cavity of gantry 112 to a position between treatment head 111 and detector 116 according to some embodiments.

Rotation of gantry 112 may cause treatment head 111, detector 116 and translation stage 125 to rotate around the isocenter of linac 110 while maintaining the relative geometric arrangement therebetween. Moreover, the fixed relationship of each radiation source 126 to each other radiation source 126 is maintained during rotation of gantry 112 and during movement of translation stage 125.

According to some embodiments, treatment head 111 rotates to a treatment position dictated by a treatment plan, and each of radiation sources 126 successively emits radiation toward the isocenter. As will be described in detail below, translation stage 125 may move between at least two successive radiation emissions in order to simulate a source array geometry which is different from the actual physical geometry of the array of radiation sources 126. Examples of such simulation according to some embodiments will be provided below.

Detector 116 acquires a projection image based on each successive emission while treatment head 111 is disposed at the treatment position. More particularly, detector 116 develops and stores charge representing radiation intensities at each location of a radiation field produced by each successive emission. Since object 140 is located between sources 126 and detector 116, the radiation intensity at a particular location represents the attenuative properties of tissues along a divergent line between the emitting source 126 and the particular location. A set of radiation intensities acquired by detector 116 in response to a particular emission may therefore comprise a two-dimensional projection image of these tissues.

Such a projection image, taken alone, is of limited use in determining a position of a particular internal target. Specifically, the target will likely be obscured by structures located between the target and radiation sources 126 and by structures located between the target and detector 116. Processor 133 of computer system 130 therefore performs digital tomosynthesis on the projection images to generate a cross-sectional image of object 140 at the isocenter. The cross-sectional image represents a particular plane of object 140 viewed from a particular perspective (e.g., the perspective of treatment head 111).

A depth resolution and a field of view of the cross-sectional image depends on a position and size of detector 116, the source array geometry simulated by translation stage 125 and radiation sources 126 during acquisition of the projection images, and a position of an imaged object (patient anatomy) relative to sources 126 and detector 116. Accordingly, in some embodiments, translation stage 125 and radiation sources 126 may be used to simulate one of several source array geometries, where each source array geometry results in a cross-sectional image having a particular depth resolution and field of view. The simulated source array geometry may therefore be selected based on a desired depth resolution and field of view.

Operator console 130 includes input device 131 for receiving instructions from an operator and output device 132, which may be a monitor for presenting operational parameters of linac 110, images acquired by detector 116, CT images used for treatment planning, cross-sectional digital tomosynthesis images, interfaces for receiving operator instructions, and/or operator alerts. According to some embodiments, output device 132 may present an alert notifying an operator of a positioning error prior to or during treatment delivery.

Input device 131 and output device 132 are coupled to processor 133 and storage 134. Processor 133 may execute program code to perform any of the determinations and generations described herein, and/or to cause linac 110 to perform any of the process steps described herein.

Storage 134 may also store program code to generate and/or modify a treatment plan according to some embodiments. Accordingly, storage 134 may also store radiation treatment plans in accordance with any currently- or hereafter-known format. The treatment plans may comprise scripts that are automatically executable by elements of room 100 to provide treatment fractions. Each beam of each fraction of each treatment plan may require treatment head 111 to be positioned in a particular manner with respect to a patient, a collimator to be configured to define a particular beam shape, and a megavoltage x-ray source to deliver a beam having a particular energy profile.

Operator console 130 may be in a room other than treatment room 100, in order to protect its operator from radiation. For example, treatment room 100 may be heavily shielded, such as a concrete vault, to shield the operator from radiation generated by linac 110.

A hardware environment according to some embodiments may include less or more elements than those shown in FIG. 1. In addition, embodiments are not limited to the devices and/or to the illustrated environment.

Figure 2A:
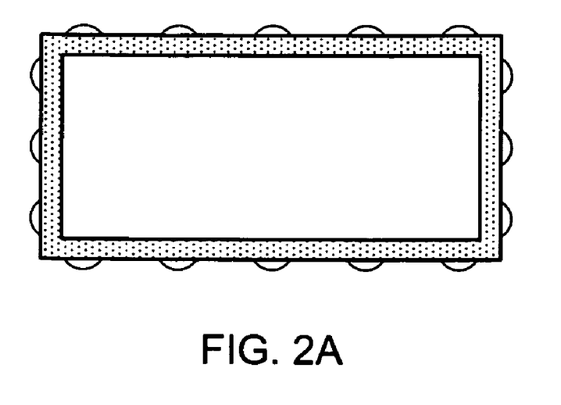
FIGS. 2A through 2C comprise top views of radiation source arrays according to some embodiments.
Figure 2B:
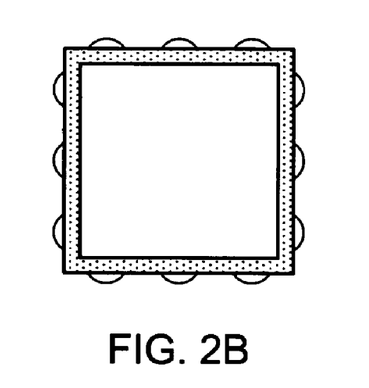
Figure 2C:
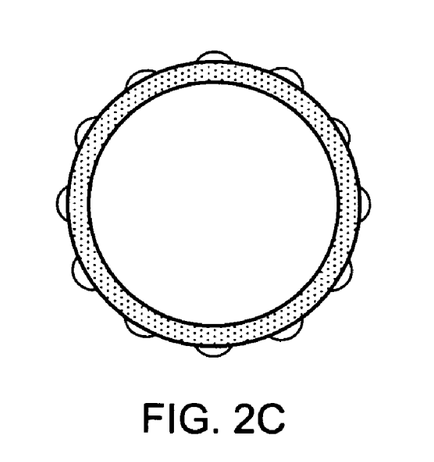

FIGS. 2A through 2C comprise top views of radiation source arrays exhibiting various geometries according to some embodiments. Each illustrated source array includes a frame and radiation sources mounted thereto. Each radiation source of an array is disposed in a fixed relationship with respect to each other radiation source of the array. The fixed relationship defines an array geometry of each array.

Each radiation source array of FIGS. 2A through 2C may be substituted for translation stage 125 and radiation sources 126 of FIG. 1. Accordingly, each radiation source array may be moved during acquisition of projection images to simulate an array geometry different from the actual geometry of the array. Digital tomosynthesis may then be performed on the projection images to create a cross-sectional image. Embodiments are not limited to the source array shapes or sizes represented in FIGS. 2A through 2C.

Figure 3:
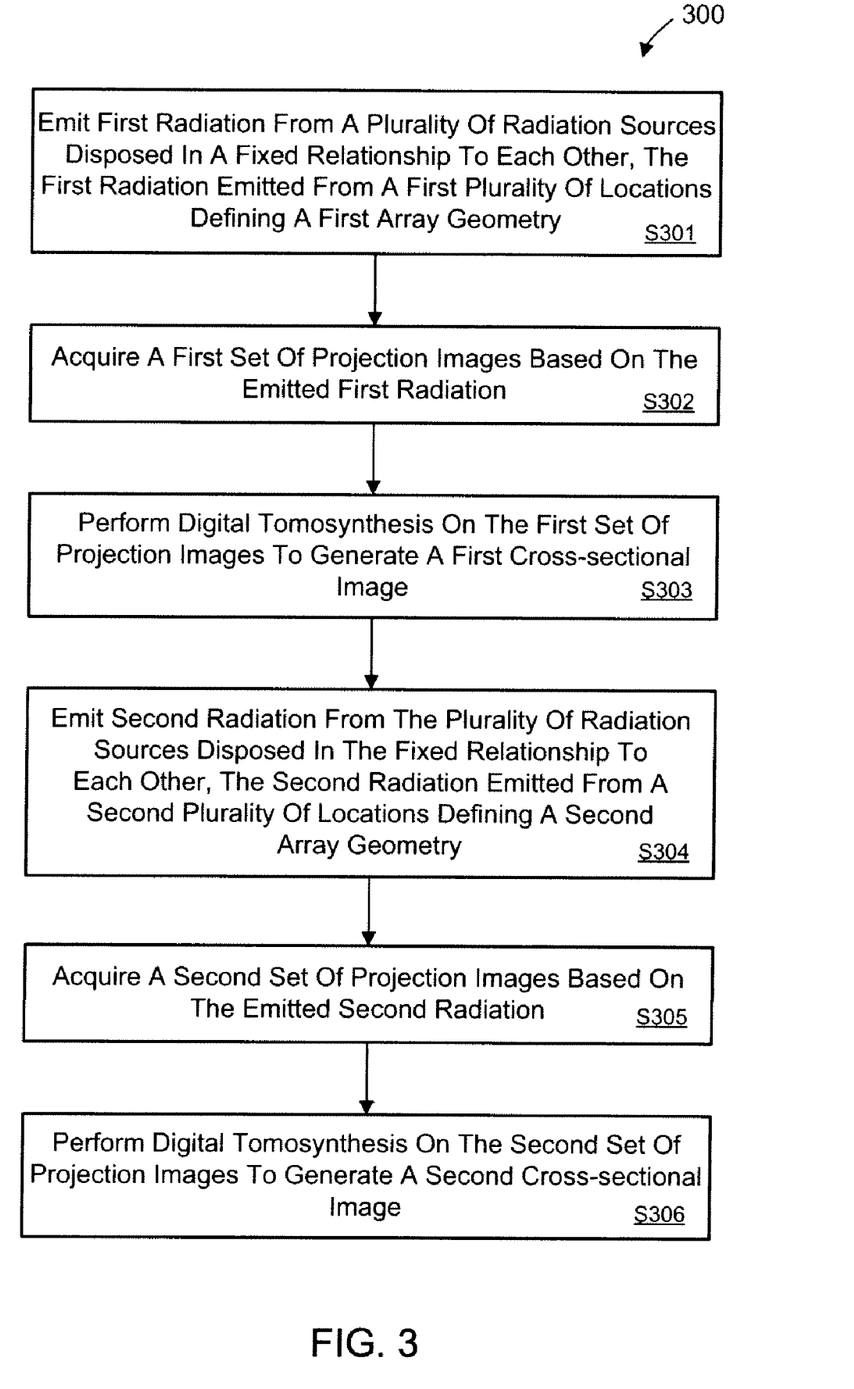
FIG. 3 comprises a flow diagram illustrating process steps according to some embodiments.

FIG. 3 is a flow diagram of a process according to some embodiments. Process 300 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 300 may be performed after a patient has been placed on a treatment table and is awaiting treatment. Prior to S301, a treatment radiation source is moved to a treatment position dictated by a treatment plan. In one example, patient 140 and linac 110 may be positioned as shown in FIG. 1 prior to S301.

The treatment plan may define multiple treatment fractions, each of which includes one or more discrete beams to be delivered. For each beam, the treatment plan may specify a gantry rotation angle, a collimator configuration, a beam profile, and a cross-sectional image of a target at a gantry isocenter and orthogonal to the beam axis. The cross-sectional image may be generated based on a CT image used to create the treatment plan At S301, first radiation is emitted from a plurality of radiation sources disposed in a fixed relationship to each other. The first radiation is emitted from a first plurality of locations defining a first array geometry. For purposes of the present example, it will initially be assumed that radiation is successively emitted at S301 from each of radiation sources 126 and from the location of each radiation source 126 shown in FIG. 1. Accordingly, the first array geometry defined by the locations is identical to the actual physical geometry of radiation sources 126.

Next, at S302, a first set of projection images is acquired based on the emitted first radiation. Detector 116 may develop, store and output a projection image corresponding to each successive emission of radiation from one of radiation sources 126. Each projection image comprises a two-dimensional set of radiation intensities representing the attenuative properties of tissues between a radiation source 126 and detector 116.

S301 and S302 may therefore be performed in conjunction with one another, in that radiation is emitted from one radiation source and a corresponding projection image is acquired, radiation is emitted from another radiation source and another corresponding projection image is acquired, and so on until radiation has been emitted from each of the plurality of radiation sources.

The projection images created at S302 may be corrected or transformed based on characteristics of detector 119 and/or based on the illustrated geometries. In the latter regard, the projection images may be modified to account for the different distances over which different portions of the emitted beams travel to reach detector 119.

Digital tomosynthesis is performed on the projection images at S303 to generate a first cross-sectional image. The cross-sectional image may be orthogonal to central beam axis 115 at the isocenter of linac 110.

Various digital tomosynthesis reconstruction algorithms have been developed, which include filtered back projection algorithms. For example, the projection images may be filtered with a Ram-Lak filter before back projection. Such algorithms are particularly suitable for digital tomosynthesis reconstruction when the radiation sources are located along an arc segment, as is the case for conventional isocentric tomography.

According to some embodiments, radiation sources 126 may be disposed in a circular configuration, an elliptical configuration, a triangular configuration, a square configuration, a rectilinear configuration, and/or along the sides of any polygon. Since radiation sources 126 in such configurations might not lie along an arc subtended from a common point, more general methods of tomosynthesis reconstruction may be employed. For example, S303 may include an iterative reconstruction method such as the algebraic reconstruction technique (ART), the simultaneous algebraic reconstruction technique (SART), the simultaneous iterative reconstruction technique (SIRT) or the ordered subsets expectation maximization (OSEM) algorithm. More generally, any methods that solve for the values of the voxels within the imaged field-of-view based on the measured projection values are suitable for tomosynthesis reconstruction. Such methods include techniques of optimization and/or regression, and may be applied to maximize certain characteristics (e.g., statistical likelihood, statistical entropy) and/or to minimize others (e.g., the sum of squared residuals).

In some embodiments, the projection images may be corrected or transformed prior to S303 based on characteristics of detector 116 and/or based on the illustrated geometries. In the latter regard, the projection images may be modified to account for the different distances over which different portions of the emitted beams travel to reach detector 116.

Digital tomosynthesis as described with respect to S301 through S303 may consume significantly less time than cone beam computed tomography, while providing a reconstructed partial cross-sectional image that is orthogonal to the principal beam axis of a megavoltage radiation source at a particular gantry angle. The reconstructed image may also include the isocenter, if the geometry of projection image acquisition is isocentric. The image could therefore be used to immediately determine whether to deliver and/or modify planned treatment based on various criteria. In comparison to two-dimensional projection images alone, digital tomosynthesis provides improved delineation of depth-resolved tissue boundaries due to the reduced influence of under-and overlying structures.

Returning to process 300, second radiation is emitted from the plurality of radiation sources at S304. The plurality of radiation sources remain disposed in the fixed relationship to each other. However, the second radiation is emitted from a second plurality of locations defining a second array geometry. The second array geometry differs from the first array geometry in size, shape, or both.

FIGS. 4A through 4D illustrate S304 according to some embodiments. Each figure shows source array 400 including twelve radiation sources and central beam axis 115. It will be assumed that the first array geometry employed at S301 is identical to the actual fixed relationship between the twelve sources of array 400. As shown, source array 400 is used to simulate second array geometry 450, which is larger than the first array geometry.

Figure 4A:
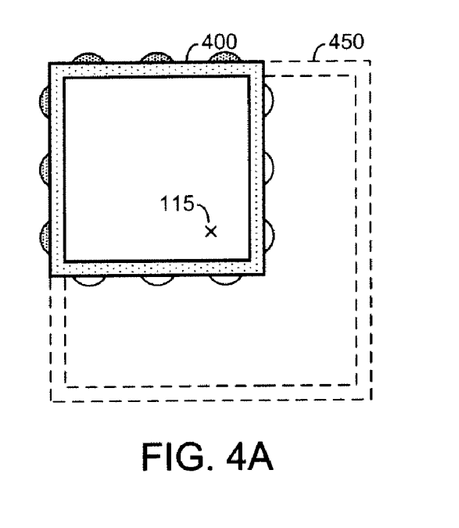
FIGS. 4A through 4D comprise top views to illustrate radiation emission to simulate a larger radiation source array with a smaller radiation source array according to some embodiments.
Figure 4B:
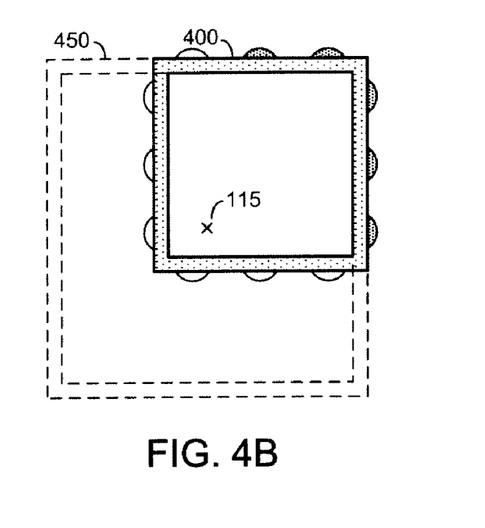
Figure 4C:
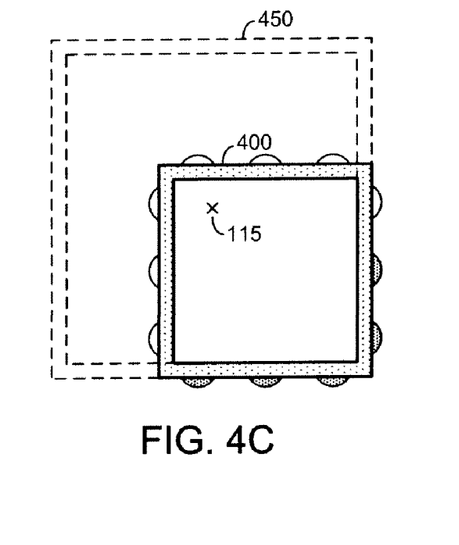
Figure 4D:
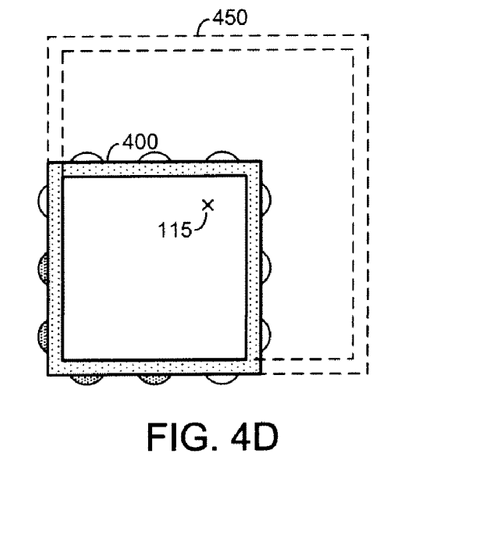

More particularly, source array 400 is moved with respect to beam axis 115 to the position shown in FIG. 4A. Radiation is then successively emitted from the location of each shaded radiation source of FIG. 4A and a projection image corresponding to each emission is acquired at S305. Source array 400 is then moved with respect to beam axis 115 to the position shown in FIG. 4B, radiation is successively emitted from the location of each shaded radiation source of FIG. 4B, and corresponding projection images are acquired. This process continues for the locations illustrated in FIGS. 4C and 4D.

Figure 5A:
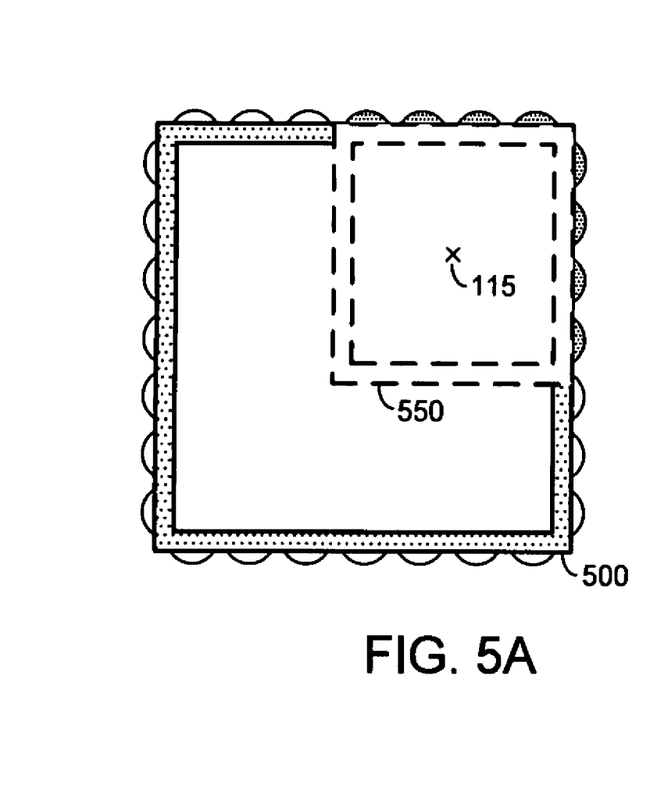
FIGS. 5A and 5B comprise top views to illustrate radiation emission to simulate a smaller radiation source array with a larger radiation source array according to some embodiments.
Figure 5B:
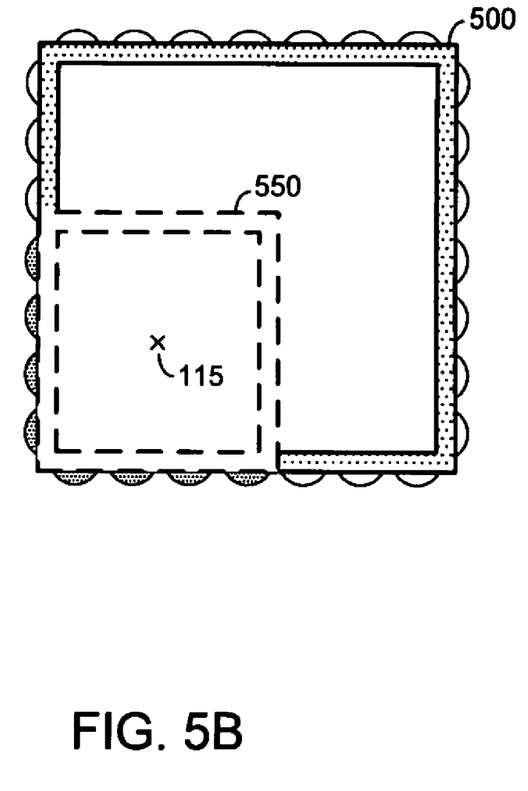

FIGS. 5A and 5B illustrate an embodiment of S304 in which source array 500 is used to simulate smaller source array geometry 550. For example, source array 500 is moved with respect to beam axis 115 to the position shown in FIG. 5A and radiation is successively emitted from the location of each shaded radiation source of FIG. 5A. Again, a projection image corresponding to each emission is acquired at S305. Source array 500 is then moved with respect to beam axis 115 to the position shown in FIG. 5B, radiation is successively emitted from the location of each shaded radiation source of FIG. 5B, and corresponding projection images are acquired.

Digital tomosynthesis is performed on the second set of projection images at S306 to generate a second cross-sectional image. Due to the differences between the first source array geometry and the second source array geometry, the second cross-sectional image may exhibit a depth resolution and field of view that differs from the depth resolution and field of view of the first cross-sectional image generated at S303. With reference to the previous examples, a cross-sectional image generated using the geometry of source array 400 will exhibit a greater field of view and less depth resolution than a cross-sectional image generated using source array geometry 450. A cross-sectional image generated using the geometry of source array 500 will, conversely, exhibit a smaller field of view and greater depth resolution than a cross-sectional image generated using the geometry of source array 550.

The first array geometry may therefore be selected in order to provide a desired field of view and a depth resolution for a given set of treatment parameters. In this regard, the first array geometry of S301 may reflect a simulated array geometry that is not identical to the actual fixed relationship between the plurality of radiation sources. The second array geometry may also be selected in order to provide a field of view and a depth resolution appropriate to a same or different set of treatment parameters.

Therapeutic radiation may be delivered to a patient between S303 and S304 according to some embodiments. For example, processor 133 may determine whether to deliver a therapeutic radiation beam according to a treatment plan based on the first cross-sectional image. This determination may include comparing the first cross-sectional image with an expected cross-sectional image generated based on the treatment plan.

The expected cross-sectional image may be generated during creation of the treatment plan. For example, a three-dimensional CT image is loaded into a treatment planning system and a treatment plan is created based on the image. A delivery vector (i.e., gantry angle) is determined for one or more treatment beams of each treatment fraction of the treatment plan. For each delivery vector, a set of projection images is generated using a divergent virtual source-detector model (e.g., such as that used for a Digitally Reconstructed Radiograph (DRR)). The set of projection images simulates the projection images described above with respect to process 300. The expected cross-sectional image for a particular delivery vector is then generated by applying digital tomosynthesis to the set of projection images generated for the particular delivery vector.

Gantry 112 may move between S303 and S304. In some examples, therapeutic radiation is delivered to a patient after S303, gantry 112 is rotated to a new position dictated by a treatment plan, and flow proceeds through S304, S305 and S306. Processor 133 may then determine to deliver a second therapeutic radiation beam to the patient according to the treatment plan based on the second cross-sectional image. Gantry 112 may remain stationary during process 300.

In some embodiments, S304 through S306 may be performed on a different day than S301 through S303, and/or with respect to a patient different from the patient imaged at S301 through S303. In the latter regard, a first source array geometry may be selected and employed at S301 through S303 based on a particular disease, site and/or anatomy of a first patient. For example, if a target or critical organ lies far from the isocenter of linac 110, it may be desirable to maximize a field of view. Accordingly, the first source array geometry may comprise a small ring.

S304 through S306 may be executed with respect to a second patient having a tumor which is near the isocenter but which is obscured by over/underlying structures. Accordingly, the second source array geometry may comprise a larger ring. In comparison to the smaller ring of the first source array geometry, the larger ring will result in a cross-sectional image having increased depth resolution but a smaller field of view.

According to some embodiments, simulation of a source array geometry also includes simulation of a source array spacing. For example, the plurality of radiation sources may be moved during S301 or S304 so as to emit radiation from locations that are spaced closer (or farther) than the actual physical spacing of the plurality of radiation sources. A greater number of unique projection images spread out over a fixed amount of coverage may result in a higher-quality cross-sectional image than a lesser number.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    emitting first radiation from a plurality of radiation sources disposed in a fixed relationship to each other, the first radiation emitted from a first plurality of locations defining a first array geometry;
    acquiring a first set of projection images based on the emitted first radiation;
    performing digital tomosynthesis on the first set of projection images to generate a first cross-sectional image;
    emitting second radiation from the plurality of radiation sources disposed in the fixed relationship to each other, the second radiation emitted from a second plurality of locations defining a second array geometry;
    acquiring a second set of projection images based on the emitted second radiation; and
    performing digital tomosynthesis on the second set of projection images to generate a second cross-sectional image,
    wherein the first array geometry and the second array geometry differ in at least one of shape and size.

2. A method according to claim 1, wherein the first array geometry is defined by the fixed relationship of the plurality of radiation sources to one another.

3. A method according to claim 2, wherein the second array geometry is smaller than the first array geometry.

4. A method according to claim 2, wherein the second array geometry is larger than the first array geometry.

5. A method according to claim 1, wherein emitting the second radiation comprises:
    successively emitting a radiation beam from one or more of the second plurality of locations;
    moving the plurality of radiation sources disposed in the fixed relationship to each other; and
    successively emitting a radiation beam from one or more other ones of the second plurality of locations, and
    wherein acquiring the second set of projection images comprises acquiring one projection image based on each radiation beam successively emitted from the second plurality of locations.

6. A method according to claim 5,
    wherein emitting the first radiation comprises:
    successively emitting a radiation beam from one or more of the first plurality of locations;
    moving the plurality of radiation sources disposed in the fixed relationship to each other; and
    successively emitting a radiation beam from one or more other ones of the first plurality of locations, and
    wherein acquiring the first set of projection images comprises acquiring one projection image based on each radiation beam successively emitted from the first plurality of locations.

7. A method according to claim 5,
    wherein acquiring the second set of projection images based on the emitted second radiation comprises:
    acquiring the second set of projection images with a radiation detector; and
    maintaining the detector in a fixed position during acquisition of the second set of projection images.

8. A method according to claim 1, further comprising:
    determining whether to deliver a therapeutic radiation beam according to a treatment plan based on the first cross-sectional image.

9. A method according to claim 8, wherein determining whether to deliver the therapeutic radiation beam comprises:
    comparing the first cross-sectional image with an expected image generated based on the treatment plan.

10. An apparatus comprising:
    an array of radiation sources disposed in a fixed relationship to each other, the array of radiation sources to emit first radiation from a first plurality of locations defining a first array geometry and to emit second radiation from a second plurality of locations defining a second array geometry;
    a translation device coupled to the array, the translation device to move the array of radiation sources disposed in the fixed relationship from the first plurality of locations defining the first array geometry to the second plurality of locations defining the second array geometry;
    a detector to acquire a first set of projection images based on the emitted first radiation and to acquire a second set of projection images based on the emitted second radiation; and
    a processor to perform digital tomosynthesis on the first set of projection images to generate a first cross-sectional image, and to perform digital tomosynthesis on the second set of projection images to generate a second cross-sectional image,
    wherein the first array geometry and the second array geometry differ in at least one of shape and size.

11. An apparatus according to claim 10, wherein the first array geometry is defined by the fixed relationship of the plurality of radiation sources to one another.

12. An apparatus according to claim 11, wherein the second array geometry is smaller than the first array geometry.

13. An apparatus according to claim 11, wherein the second array geometry is larger than the first array geometry.

14. An apparatus according to claim 10, the array of radiation sources to successively emit a radiation beam from one or more of the second plurality of locations,
- the translation device to move the plurality of radiation sources disposed in the fixed relationship to each other; and
- the array of radiation sources to successively emit a radiation beam from one or more other ones of the second plurality of locations.

15. An apparatus according to claim 14,
- the array of radiation sources to successively emit a radiation beam from one or more of the first plurality of locations,
- the translation device to move the plurality of radiation sources disposed in the fixed relationship to each other; and
- the array of radiation sources to successively emit a radiation beam from one or more other ones of the first plurality of locations.

16. An apparatus according to claim 14,
- wherein the detector is maintained in a fixed position during acquisition of the second set of projection images.

17. An apparatus according to claim 10, the processor further to:
- determine whether to deliver a therapeutic radiation beam according to a treatment plan based on the first cross-sectional image.

18. An apparatus according to claim 17, the processor further to:
- compare the first cross-sectional image with an expected image generated based on the treatment plan.

\* \* \* \* \*